United States Patent [19]
Wilson et al.

[11] Patent Number: 6,030,349
[45] Date of Patent: Feb. 29, 2000

[54] MEDICAL GUIDE WIRE TORQUER

[75] Inventors: John Wilson, Minnetonka; Thomas Carlson, Eden Prairie, both of Minn.

[73] Assignee: CarTika Medical, Inc., Plymouth, Minn.

[21] Appl. No.: 09/027,712

[22] Filed: Feb. 23, 1998

[51] Int. Cl.[7] .................................................. A61B 5/00
[52] U.S. Cl. .......................................... 600/585; 600/434
[58] Field of Search .................................. 600/434, 585; 604/159

[56] References Cited

U.S. PATENT DOCUMENTS

| | | | |
|---|---|---|---|
| 4,615,472 | 10/1986 | Nash | 600/434 |
| 4,726,369 | 2/1988 | Mar | 600/434 |
| 4,858,810 | 8/1989 | Intlekofer et al. | 226/127 |
| 4,860,742 | 8/1989 | Park et al. | 604/159 |
| 4,957,117 | 9/1990 | Wysham | 604/95 |
| 4,973,329 | 11/1990 | Park et al. | 606/1 |
| 5,137,288 | 8/1992 | Starkey et al. | 604/159 |
| 5,137,517 | 8/1992 | Loney et al. | 604/159 |
| 5,161,534 | 11/1992 | Berhiaume | 600/434 |
| 5,219,332 | 6/1993 | Nelson et al. | 600/585 |
| 5,312,338 | 5/1994 | Nelson et al. | 604/95 |
| 5,325,746 | 7/1994 | Anderson | 81/487 |
| 5,325,868 | 7/1994 | Kimmelstiel | 600/434 |
| 5,423,331 | 6/1995 | Wysham | 600/585 |
| 5,579,780 | 12/1996 | Zadini et al. | 600/585 |
| 5,606,980 | 3/1997 | Calhoun et al. | 600/585 |
| 5,634,475 | 6/1997 | Wolvek | 600/585 |
| 5,666,970 | 9/1997 | Smith | 600/585 |

*Primary Examiner*—Cary O'Connor
*Assistant Examiner*—Charles Marmor, II
*Attorney, Agent, or Firm*—Edwin E. Voigt, II, Esq.; Vidas, Arrett & Steinkraus

[57] ABSTRACT

A medical guide wire torquer is disclosed which is adapted for one-handed convenient attachment, release, and re-attachment to a medical guide wire utilized during medical procedures. The guide wire torquer has a body having ends and positioners integral or affixed to each end, a first channel, and an internal cavity. At least one elastomer is positioned within the internal cavity. A button is positioned within the cavity for engagement to the elastomer where the button extends beyond the body. The button includes a pair of retainers adapted for engagement to the positioners and a second channel adapted for alignment with the first channel during the release of a guide wire. A guide wire is releasably grasped by the vertical movement of the button within the cavity which causes the expansion of the elastomers which, in turn, results in a binding of the guide wire between the first and second channels.

32 Claims, 4 Drawing Sheets

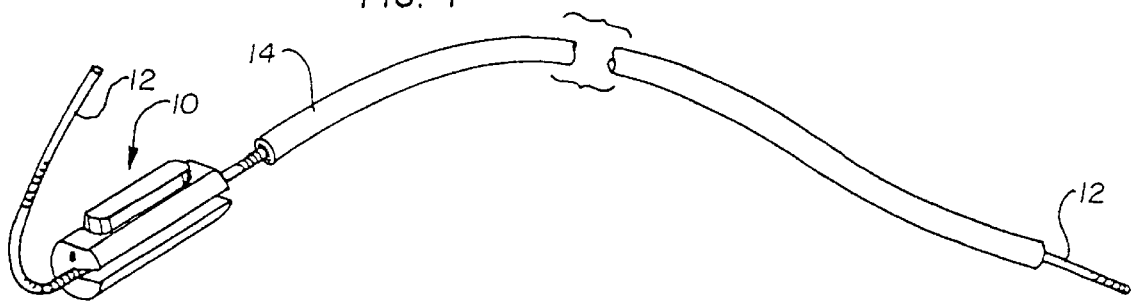
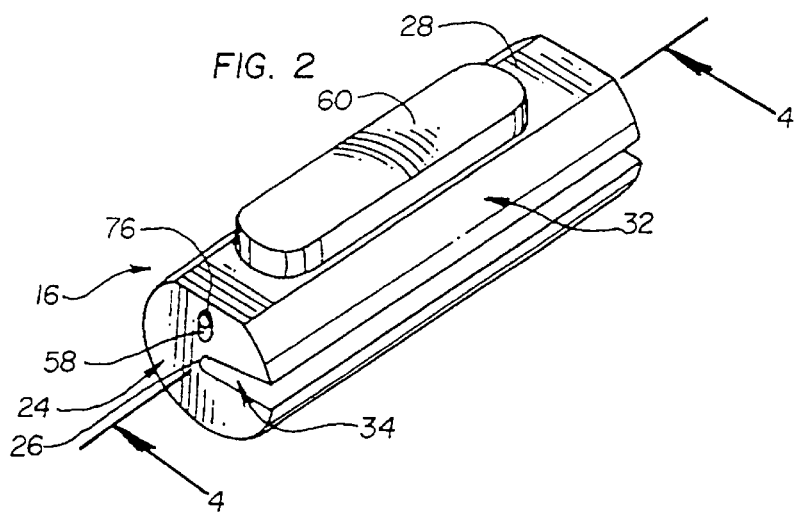
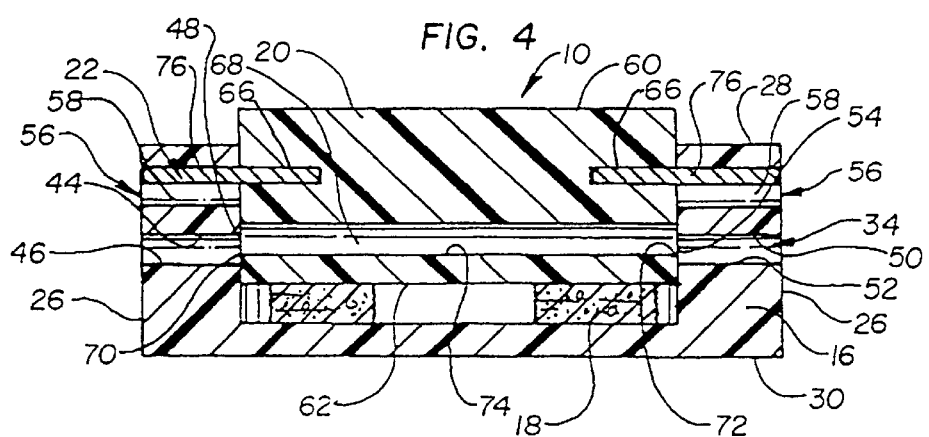

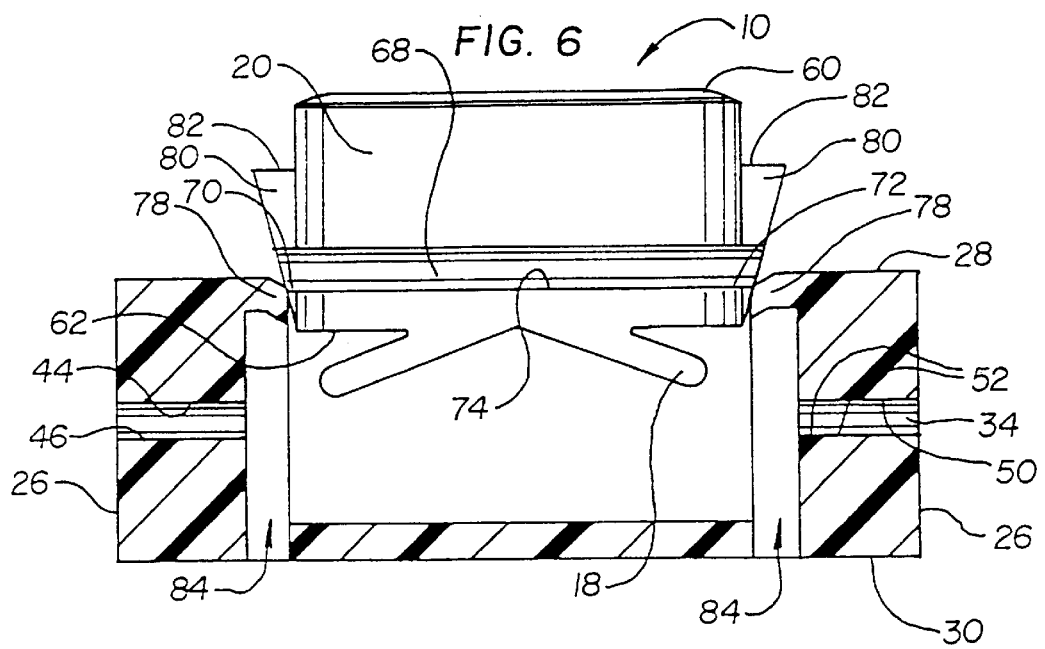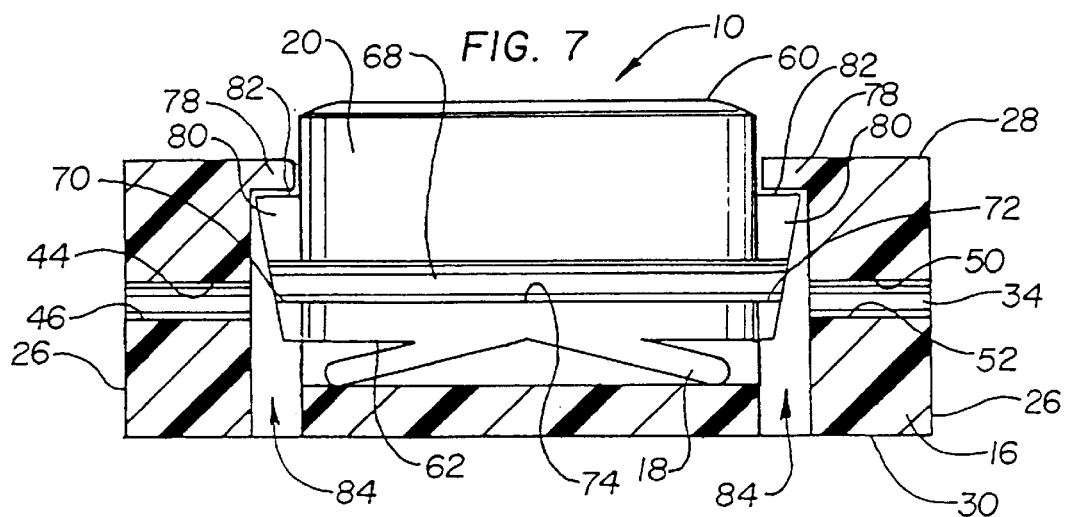

MEDICAL GUIDE WIRE TORQUER

BACKGROUND

Medical guide wire grasping devices have been attempted in the past. The principal drawback of these devices is the failure of the devices to be user-friendly during critical periods of a medical procedure. A physician is therefore required to expend needless time, exertion, and/or concentration on the manipulation of a medical guide wire grasping device and/or medical guide wire during a medical procedure. The known devices have, in turn, caused physicians to become frustrated and/or unsatisfied with the grasping devices as known. In addition, the known guide wire grasping devices have increased the risk of potentially adverse complications to a patient due to the inability of a physician to satisfactorily grasp and manipulate a medical guide wire during a procedure.

The known guide wire grasping devices have also failed to incorporate a convenient feature for loading of a guide wire into or through the device. These devices have required a physician to twist the device and/or guide wire together for affixation. Conversely, to change the position of a device relative to the guide wire during a procedure, a physician was required to stop the procedure and untwist the guide wire from the device for re-attachment at a desired location. Significant time loss thereby occurred during the medical procedure, necessitating a patient to be exposed to anesthetics for an additional period of time which may otherwise have been avoided.

In addition, the devices attempted in the past have necessitated a medical provider to disassemble the device from a guide wire for repositioning on the guide wire or removal from the guide wire. The utility of these devices during a medical procedure was thereby significantly reduced.

Further, the devices attempted in the past were frequently quite small in diameter, causing difficulty in controlling of the device or guide wire while a medical provider was wearing sterile gloves. The small diameter of these devices caused the "bunching" or "rolling" of a physician's sterile gloves when the devices were rotated during a medical procedure. The medical provider/physician thereby had difficulty controlling and grasping the device during a procedure.

The devices attempted in the past also failed to provide an easy to recognize release/relocation feature identifiable by touch, which eliminated the necessity for the physician to remove his or her eyes from a patient or monitor during the manipulation of a guide wire. During critical periods within a medical procedure, a physician is required to simultaneously release/relocate a grasping device from a guide wire and maintain observation of a patient. The devices attempted in the past failed to enable a physician to continuously observe a patient while simultaneously relocating the device on a guide wire.

The devices attempted in the past also failed to provide for convenient use during the exchange of guide wires of varying diameter dimensions. These devices were required to be disassembled and/or unscrewed from a guide wire when substitute diameter guide wires were desired during a medical procedure. The utility of these devices was thereby significantly reduced.

The devices attempted in the past also failed to provide for convenient slip-free grasping by a medical provider during a procedure. The known devices, frequently due to size, materials, and/or texture, became slippery and difficult to grasp if exposed to bodily fluids during a medical procedure. The utility of these devices was thereby significantly reduced.

The medical guide wire torquing device described and disclosed herein overcomes these and other identifiable drawbacks of the guide wire grasping devices as known.

SUMMARY

A medical guide wire torquer is disclosed which is adapted for one-handed convenient attachment, release, and re-attachment to a medical guide wire utilized during medical procedures. The guide wire torquer has a body having ends and positioners integral or affixed to each end, a first channel, and an internal cavity. At least one elastomer is positioned within the internal cavity. A button is positioned within the cavity for engagement to the elastomer where the button extends beyond the body. The button includes a pair of retainers adapted for engagement to the positioners and a second channel adapted for alignment with the first channel during the release of a guide wire. A guide wire is releasably grasped by the vertical movement of the button within the cavity which causes the expansion of the elastomers which, in turn, results in a binding of the guide wire between the first and second channels.

It is a principal object of the present invention to provide a medical guide wire torquing device of relatively simple and inexpensive design, construction, and operation which is safe and which fulfills the intended purpose of being easily engaged to, and repositioned on, a medical guide wire without fear or risk of injury to persons and/or damage to property during a medical procedure.

It is another principal object of the present invention to provide a medical guide wire torquing device which is "user friendly" to a physician during a medical procedure.

It is still another principal object of the present invention to provide a medical guide wire torquing device which reduces the risk of complications to a patient associated with the use of a medical guide wire during medical procedures.

It is still another principal object of the present invention to provide a medical guide wire torquing device which does not require disassembly or unscrewing for attachment to, relocation on, or disassembly from a medical guide wire.

It is still another principal object of the present invention to provide a medical guide wire torquing device which includes a release feature which may be easily recognized by a physician to the touch, eliminating the necessity for the physician to terminate observation of a patient during a medical procedure requiring the use of a guide wire.

It is still another principal object of the present invention to provide a medical guide wire torquing device which may be easily relocated on a guide wire or attached to another guide wire of varying diameter dimensions during use within a medical procedure.

It is still another principal object of the present invention to provide a medical guide wire: torquing device which is of a convenient size for grasping which does not cause "bunching" or "rolling" of surgical gloves.

It is still another principal object of the present invention to provide a medical guide wire torquing device which is convenient to grasp which does not become slippery if exposed to bodily fluids during a medical procedure.

A feature of the medical guide wire torquer includes a body having a pair of ends, each end having a positioner, the body additionally having a first channel and an internal cavity.

Another feature of the medical guide wire torquer is a pair of elastomers positioned in the cavity.

Still another feature of the medical guide wire torquer is a button positioned in the cavity.

Still another feature of the medical guide wire torquer is a button having a surface extending beyond the body, a pair of retainers, each retainer adapted for engagement to one of the positioners, and a second channel adapted for alignment with the first channel during depression of the button and compression of the elastomers.

Still another feature of the medical guide wire torquer is the grasping and/or binding of a medical guide wire between the first and second channels upon the release of the button and the expansion of the elastomers.

Still another feature of the medical guide wire torquer is the provision of the elastomers integral to the button.

Still another feature of the medical guide wire torquer is the provision of an exterior textured grasping surface which facilitates grasping if exposed to bodily fluids during a medical procedure.

BRIEF DESCRIPTION OF THE DRAWINGS

FIG. 1 is an environmental view of the guide wire torquing device.

FIG. 2 is an isometric view of the guide wire torquing device.

FIG. 4 is a cross-sectional side view of the guide wire torquing device taking along the line 4—4 of FIG. 2.

FIG. 6 is an alternative cross-sectional side view of the guide wire torquing device during positioning of the button within the cavity.

FIG. 7 is an alternative cross-sectional side view of the guide wire torquing device taken along the line 4—4 of FIG. 2.

SPECIFICATION

Figure 3:
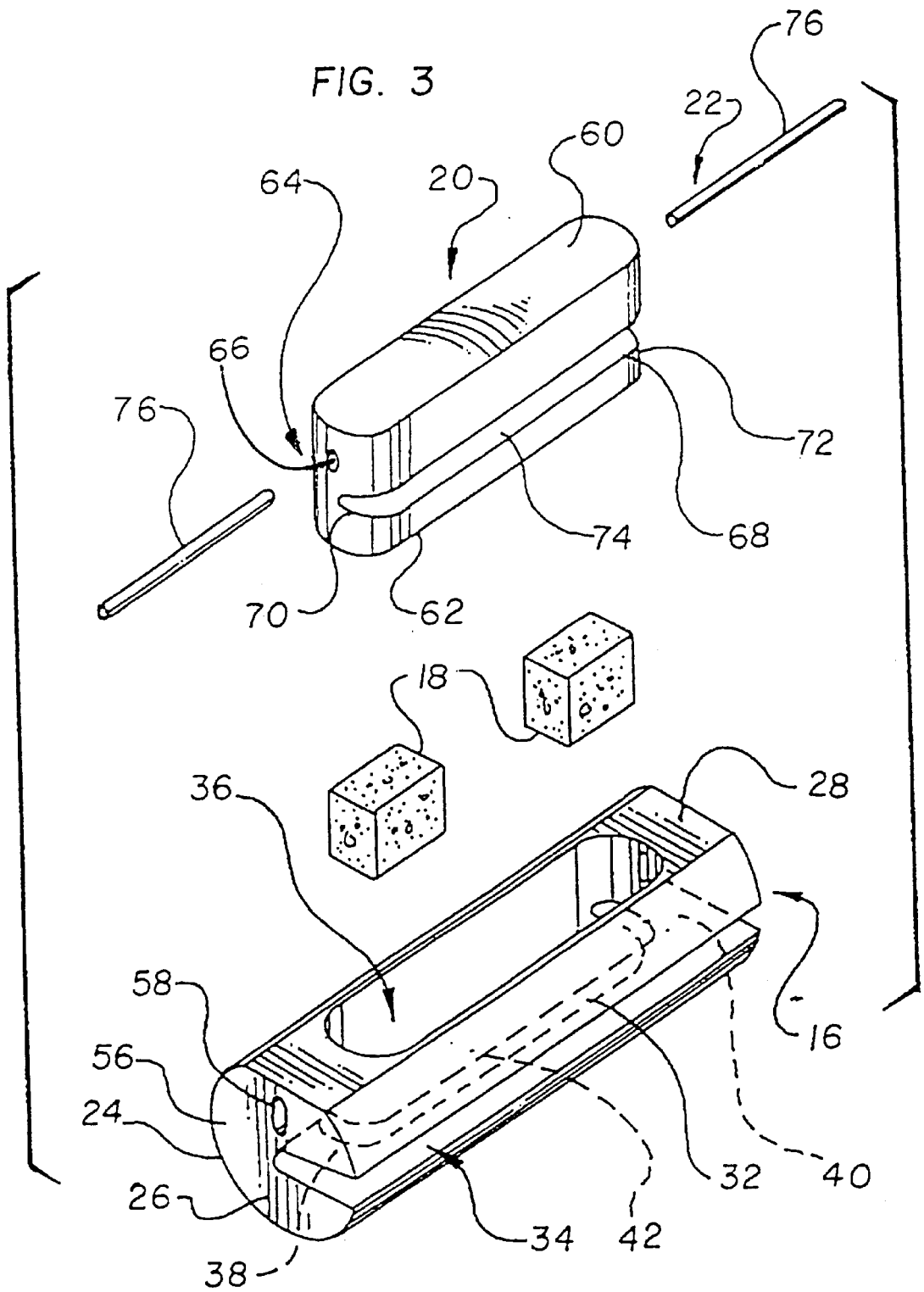
FIG. 3 is an exploded partial phantom line isometric view of the guide wire torquing device.

In general, the medical guide wire torquer is described herein. The medical guide wire torquer, in general, is indicated by the numeral 10. The medical guide wire torquer 10 is preferably adapted for engagement to a medical guide wire 12 which may be surrounded by a sheath 14. (FIG. 1) In general, the medical guide wire torquer 10 includes a body 16, an elastomer 18, a button 20, and a fastener 22.

The medical guide wire torquer 10 is preferably used with a guide wire 12 having a size ranging between ten to thirty-eight, as identified in the medical industry, dependent upon the vascular size of a patient and/or the medical procedure to be practiced.

As may be seen in FIGS. 1–7, the body 16 is preferably elongate and substantially cylindrical in shape. The body 16 preferably includes a pair of ends 24 which may be substantially vertical end walls 26. It should be noted that the body 16 may be formed in alternative shapes at the discretion of an individual, including, but not limited to, rectangular and/or oval, or any other shape as preferred by an individual, provided that the essential functions, features, and attributes described herein are not sacrificed.

The body 16 may be preferably formed of molded plastic material. Alternatively, the body 16 may be formed of any other material as desired by an individual, including metal. It should be noted that the body 16 may be formed of a material which may be repeatedly sterilized by medical providers for re-use during medical procedures. Alternatively, the body may be initially sterilized for disposal following use as desired by an individual.

The body 16 may include a top surface 28 and a bottom surface 30 at the discretion of an individual. The top surface 28 may be preferably flat to facilitate ease of grasping by a medical provider.

The body 16 may also preferably include a central body portion 32 which may include a first channel 34. The first channel 34 preferably extends the entire length of the body 16 between the pair of ends 24 or end walls 26. The first channel 34 is preferably position approximately equal distances between the top surface 28 and bottom surface 30 of the body 16.

The first channel 34 may include a first ledge 38, a second ledge 40, and a cutaway portion 42. The first ledge 38, second ledge 40, and cutaway portion 42 are defined by the shape of the internal cavity 36 as traversing the first channel 34.

The body 16 also preferably includes an internal cavity 36 which extends vertically downward from the top surface 28 toward the bottom surface 30. The internal cavity 36 preferably traverses the top surface 28 but does not traverse the bottom surface 30.

The first ledge 38 preferably includes a first upper surface 44, a first lower surface 46, and a first interior edge 48. (FIGS. 3–4) The second ledge 40 preferably includes a second upper surface 50, a second lower surface 52, and a second interior edge 54. (FIGS. 3–4)

Each of the pair of ends 24 preferably includes a positioner 56 which may be a slot 58 as depicted in FIGS. 2–3. The positioner 56 preferably functions to assist in the retention of the button 20 in a desired location relative to the body 16.

It should be noted that the positioner 56 may be formed in the shape of a channel or tongue for engagement to a groove as integral to the body 16 at the preference of an individual. It should also be noted that the body 16 may include an internal stop within the cavity 36 for limiting the vertical movement of the button 20 to prevent separation from the body 16 as desired by an individual.

The first channel 34 preferably is adapted for receiving engagement of the medical guide wire 12 during use of the medical guide torquer 10. The internal cavity 36 preferably functions for receiving engagement of the button 20 and elastomers 18 and further provides for a convenient grasping surface by a medical provider during use of the medical guide torquer 10 during a medical procedure. The first ledge 38 and second ledge 40 preferably function as the areas for releasable affixation of the medical guide wire 12 in conjunction with the button 20 during use of the medical guide wire torquer 10.

The exterior of the body 16 may include a non-slip or textured grasping surface which may be knurled at the discretion of an individual to prevent slippage within a medical provider's hands or gloves upon exposure to bodily fluids during a medical procedure.

At least one elastomer 18 is preferably positioned within the cavity 36 proximate to the bottom 30. A plurality of elastomers 18 may be positioned in the cavity 36 at the discretion of all individual provided that the essential functions, features, and attributes described herein are not sacrificed. The elastomers 18 are preferably rectangular in shape, however the elastomers 18 may be elongate, cylindrical, square, or any other shape as desired by an individual provided that the essential functions, features, and attributes described herein are not sacrificed.

The elastomers 18 are preferably formed of rubber material which may have any desired density as preferred by an individual for the provision of repeated compression and expansion during use of medical guide torquer 10.

It should be noted that the elastomer 18 may be positioned proximate, adjacent, or in contact to the bottom 30 of the cavity 36 as desired by an individual. The elastomers 18 preferably function to alternatively compress and expand, permitting the adjustable positioning of the button 20 within the cavity 36.

The elastomers 18 may be separate and independent from the button 20 or may be integral to the button 20 as desired by an individual.

The elastomers in the preferred embodiment are preferably pads of hard rubber material. Alternatively, the elastomers 18 may be formed of leaf springs or coil springs at the discretion of an individual, provided that the elastomers 18 function to provide a desired compression/expansion force during the vertical positioning of the button 20 within the cavity 36.

The button 20 is preferably positioned within, and vertically adjustable, relative to the cavity 36 of the body 16. The button 20 preferably includes an exterior surface 60 which extends beyond the top surface 28 of the body 16. The button 20 also preferably includes an undersurface 62 which is preferably adjacent, proximate to, and engages the elastomers 18.

The exterior surface 60 preferably extends outwardly beyond the to surface 28 of the body 16 to enable a physician or other medical provider to identify the button 20 by touch, without necessitating the medical provider to visualize the button 20 during use of the medical guide wire torquer 10. The undersurface 62 of the button 20 preferably functions as a base for contact with, and compression of, the elastomers 18 during the depression of the button 20 during use of the medical guide wire torquer 10.

The opposite ends of the button 20 preferably each include a retainer 64. Each of the retainers 64 are preferably adapted for positioning adjacent to, and in alignment with, a positioner 56. The pair of retainers 64 may be apertures 66 at the discretion of an individual. Alternatively, the retainers 64 may be tongues for engagement to the grooves of the positioners 56 at the discretion of an individual.

The button 20 preferably includes a second channel 68 which is preferably adapted for positioning proximate to the first channel 34. The second channel 68 preferably includes a leading edge 70 which is preferably positioned proximate to the first interior edge 48 of the first ledge 38. The second channel 68 also preferably includes a trailing edge 72 which is preferably positioned proximate to the second interior edge 54 of the second ledge 40. The second channel 68 also preferably includes a substantially flat base surface 74.

The second channel 68 is preferably adapted for alignment with the first channel 34 during receiving engagement to a medical guide wire 12 upon the depression of the button 20. Upon the release of the button 20, and expansion of the elastomers 18, the leading edge 70 and trailing edge 72 actuate vertically for binding of a medical guide wire 12 to the first interior edge 48 and second interior edge 54 of the first ledge 38 and second ledge 40 for affixation of a medical guide wire 12 in a desired location.

Figure 5A:
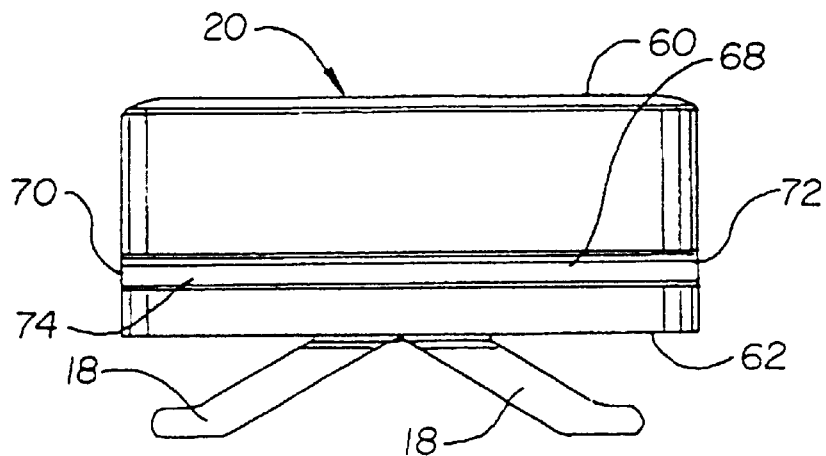
FIGS. 5a–5c are alternative detail views of the button of the guide wire torquing device.
Figure 5B:
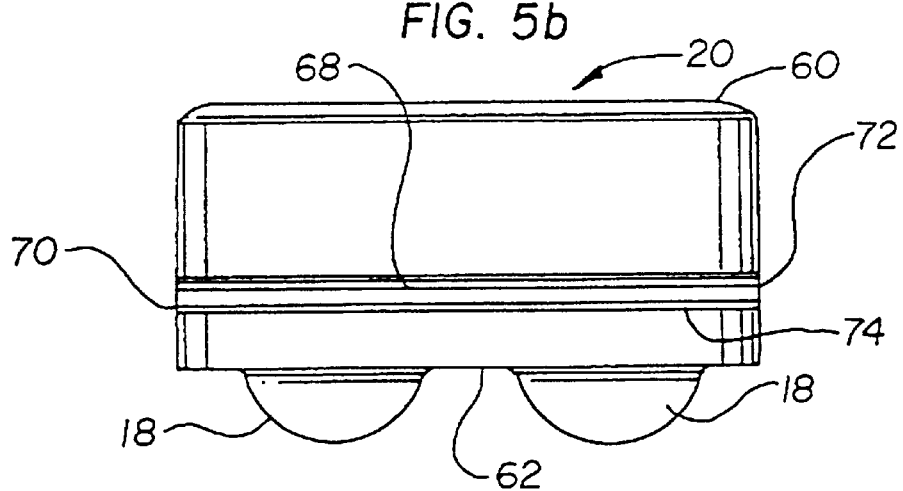
Figure 5C:
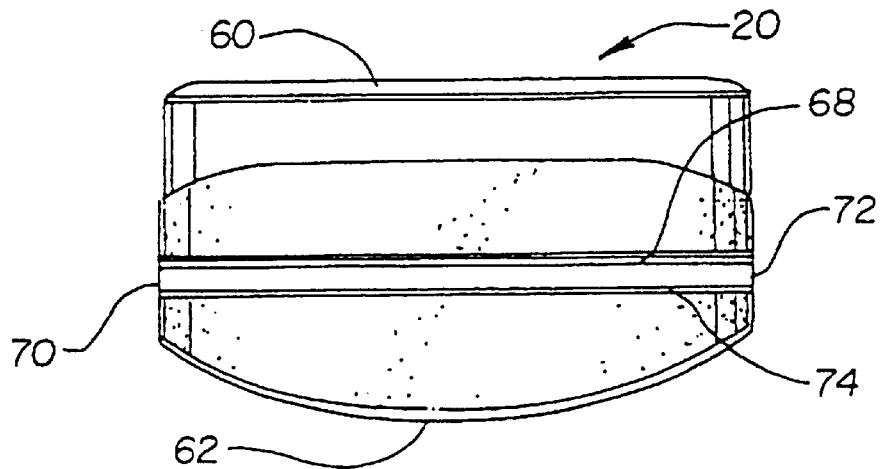

The button 20 may be formed of a same material as the body 16 at the discretion of a individual. Alternatively, the button 20 may be formed of hard rubber or plastic and include integral elastomers 18 extending downwardly from the undersurface 62 as depicted in FIGS. 5a–5c. Alternatively, a leaf spring or coil spring may be integral to the undersurface 62 of the button 20 for engagement to the bottom surface 30 within the internal cavity 36. Alternatively, the button 20 may be formed of a hard resiliently flexible rubber material having a tapered design as depicted in FIG. 5c. In this configuration, the undersurface of the button 20 compresses and expands during the downward compression and vertical release of the button 20 during use of the medical guide wire torquer 10.

A fastener 22 preferably connects the button 20 to the body 16. The fastener 22 also preferably permits the adjustable vertical positioning of the button 20 relative to the body 16 within the cavity 36. The fastener 22 may be a pin 76 positioned within each aperture 66 and each slot 58 as depicted in FIGS. 2, 3, and 4. The fastener 22 and/or pins 76 preferably enable the vertical positioning of the button 20 relative to the body 16 upon compression or expansion of the elastomers 18 during use of the medical guide wire torquer 10. The pins 76 also preferably function to retain the button 20 in alignment with the body 16 during the adjustable vertical positioning of the pins 76 within the respective slots 58 during use of the medical guide wire torquer 10.

In operation, the medical guide wire torquer 10 preferably has a grasping position where the elastomers 18 are expanded as defined by the positioning of the leading edge 70 of the second channel 68 proximate and elevated with respect to the first interior edge 48 of the first ledge 38 of the first channel 34; and the positioning of the trailing edge 72 of the second channel 68 proximate and elevated with respect to the second interior edge 54 of the second ledge 40 of the first channel 34.

In this configuration, the medical guide wire 12 is preferably in flush engagement with the base surface 74 of the second channel 68 and binding occurs by sandwiching and/or pinching of the medical guide wire 12 between the base surface 74 and the leading edge 70 with the first interior edge 48 and first upper surface 44 of the first ledge 38; simultaneously binding, sandwiching, or pinching of the medical guide wire 12 occurs between the base surface 74 and trailing edge 72 of the second channel 68 with the second interior edge 54 and second upper surface 50 of the second ledge 40. It should be noted that the grasping position for the medical guide wire torquer 10, in this position, is the at-rest position, where the button 20 is released by an individual and the elastomers 18 are permitted to obtain the maximized natural expanded state or configuration whereupon the exterior surface 60 of the button 20 extends upwardly from the top surface 28 of the body 16.

The grasping position enables a medical provider to recognize the location of the button 20 with one hand, eliminating the necessity for visual observation of the medical guide wire torquer 10. The grasping position binds a medical guide wire 12 for rotation or manipulation without slippage or inadvertent release, significantly improving the utility of the medical guide wire torquer 10 and the safety of a patient. The grasping position of the medical guide wire torquer 10 permits rotation of a medical guide wire 12 without the rolling or bunching of sterile gloves by a medical provider. In addition, the grasping position of the medical guide wire torquer 10 provides a non-slip surface for grasping by an individual if exposed to bodily fluids, further enabling a physician to continuously observe a patient without the necessity to observe the medical guide wire torquer 10 during use.

The medical guide wire torquer 10 includes a release position where the elastomers 18 are compressed. This position is defined by the positioning of the leading edge 70 of the second channel 68 proximate to, and in substantial alignment with, the first interior edge 48 of the first ledge 38 of the first channel 34 and the simultaneous positioning of the trailing edge 72 of the second channel 68 proximate to, and in substantial alignment with, the second interior edge 54 of the second ledge 40 of the first channel 34.

In this configuration, the medical guide wire 12 is preferably released from the binding, sandwiching, and/or pinching between the first channel 34 and the second channel 68 and is preferably freely movable with respect to the medical guide wire torquer 10. Alternatively, the separation of the medical guide wire torquer 10 from the medical guide wire 12 may occur simply by the withdrawal of the guide wire 12 horizontally outwardly away from the first and second channel 34, 68 respectively. It should be noted that the release position for the medical guide wire torquer 10 occurs only when force or work is applied or exerted for compression of the button 20 relative to the body 16 which, in turn, causes the compression of the elastomers 18. Release of the button 20 then permits the expansion of the elastomers 18 for manipulation of the button 20 vertically outwardly within the cavity 36 for acquisition of the at-rest position. It should be noted that in the release position, the exterior surface 60 of the button 20 is substantially flush with the top surface 28 of the body 16.

The release position of the medical guide wire torquer 10 permits the fast and convenient separation of a medical guide wire 12 from a medical guide wire torquer 10 by depression of the button 20. The release position also enables a medical provider or physician to reposition the medical guide wire torquer 10 on a medical guide wire 12 at a desired location without disassembly or unscrewing to accomplish repositioning. The release position of the medical guide wire torquer 10 also enables a medical provider/physician to easily substitute another guide wire 12 having a different diameter dimension quickly and easily without disassembly or unscrewing of the medical guide wire torquer device 10

In an alternative embodiment as depicted in FIGS. 6 and 7, the positioners 56 of the body 16 may be formed of shelves 78 which in turn may be resiliently pliable during the initial receipt of, and engagement to, the button 20. It should be noted that the shelves 78 are preferably resiliently pliable in one direction only toward the bottom surface 30. In this embodiment, the button 20 preferably includes a pair of tabs 80 which may be angularly or wedge-shaped to facilitate positioning within the cavity 36. Each of the tabs 80 preferably include a horizontal stop 82 which is adapted for positioning proximate to or is adapted for engagement with the underside of a respective shelf 78 when the button 20 is in the grasping position. The shelves 78 preferably assume a substantially horizontal position or configuration with respect to the body 16 upon the passing of the stop 82 within the cavity 36.

Further, as depicted in FIGS. 6 and 7, the undersurface 26 of the button 20 preferably includes integral elastomers 18 which may be leaf springs, coil springs and/or formed of resiliently flexible rubber material at the preference of an individual. The embodiment depicted in FIGS. 6 and 7 further may include molding apertures 84 which may be utilized to facilitate the manufacture of the body 16 at the discretion of an individual. In operation, the embodiment as depicted in FIGS. 6 and 7 functions identically to the embodiment as earlier described for the grasping and release of a medical guide wire 12 with the exception of the absence of the pins 76 and the slots 58.

The medical guide wire torquer 10 is preferably originally sterilized and packaged for use by a medical provider. The medical guide wire torquer 10 may be disposable or reusable at the discretion of an individual. The component parts of the body 16, button 20, elastomers 18, and fasteners 22 are preferably selected from sufficiently durable materials which will not degrade upon repeated sterilization procedures, where the performance of the medical guide wire torquer 10 will not be adversely affected by repeated sterilization procedures. Preferably, the medical guide wire torquer 10 will have a desired useful life even upon repeated exposure to sterilization fluids and/or temperatures.

The present invention may be embodied in other specific forms without departing from the spirit or essential attributes thereof, therefore, the illustrated embodiment should be considered in all respects as illustrative and not restrictive, reference being made to the appended claims rather than to the foregoing description to indicate the scope of the invention.

We claim:

1. A medical guide wire torquer comprising:

(a) a body having a pair of ends, each of said ends having a positioner, said positioner comprising a slot, said body further having a top and a bottom, a central body portion having a first channel, and an internal cavity;

(b) at least one elastomer positioned in said cavity, said elastomer positioned proximate to said bottom; and (c) a button positioned in said cavity, said button having an upper surface extending beyond said body, said button extending outward from said top, said button comprising a lower surface, said lower surface engaging said elastomer, a pair of retainers, each of said retainers being adjacent and engaged to one of said positioners, and a second channel proximate to said first channel, said pair of retainers comprising apertures adapted for alignment with one of said slots.

2. The medical guide wire torquer of claim 1, further comprising a fastener connecting said button to said body and positioning said button within said cavity.

3. The medical guide wire torquer of claim 2, said ends further comprising end walls.

4. The medical guide wire torquer of claim 3, said first channel further comprising a first ledge, a second ledge, and a central cutaway portion.

5. The medical guide wire torquer of claim 4, wherein said internal cavity extends from said top into said central body portion.

6. The medical guide wire torquer of claim 5, wherein said first channel is positioned approximately equal distances between said top and said bottom.

7. The medical guide wire torquer of claim 6, further comprising a plurality of elastomers disposed in said cavity proximate to said bottom.

8. The medical guide wire torquer of claim 7, wherein said elastomers alternatively compress and expand, permitting adjustable positioning of said button within said cavity.

9. The medical guide wire torquer of claim 8, said second channel comprising a leading edge proximate to said first ledge and a trailing edge proximate to said second ledge.

10. The medical guide wire torquer of claim 9, wherein said button has a grasping position when said elastomers are expanded, defined by the positioning of the leading edge of the second channel proximate to, and elevated with respect to the first ledge of the first channel and the positioning of the trailing edge of the second channel proximate to, and elevated with respect to the second ledge of the first channel.

11. The medical guide wire torquer of claim 10, wherein said button has a release position when said elastomers are compressed, defined by the positioning of the leading edge of the second channel proximate to, and in substantial alignment with, the first ledge of the first channel and the positioning of the trailing edge of the second channel proximate to, and in substantial alignment with, the second ledge of the first channel.

12. The medical guide wire torquer of claim 11, wherein said elastomers are expanded at an at-rest position, thereby positioning the button in a grasping position relative to the body.

13. The medical guide wire torquer of claim 12, said fastener further comprising a pin positioned in each of said apertures, each of said pins being adjustably positioned in one of said slots.

14. The medical guide wire torquer of claim 13, wherein said first channel and said second channel are adapted to releasably engage said medical guide wire.

15. The medical guide wire torquer of claim 14, wherein said body is elongate being substantially cylindrical in shape.

16. The medical guide wire torquer of claim 15, said body further comprising an exterior textured grasping surface.

17. A medical guide wire torquer comprising:

(a) a body having a pair of ends, each of said ends having a slot, said body further having a top, a bottom, a central body portion having a first channel, and an internal cavity;

(b) a t least one elastomer positioned in said cavity proximate to said bottom;

(c) a button positioned in said cavity, said button having an upper surface extending above said top, a lower surface engaging said elastomer, a pair of apertures, each of said apertures being aligned with one of said slots, and a second channel proximate to said first channel; and (d) a fastener connecting said button to said body and positioning said button within said cavity.

18. The medical guide wire torquer of claim 17, wherein said elastomer is integral to said button.

19. The medical guide wire torquer of claim 17, said ends further comprising end walls.

20. The medical guide wire torquer of claim 19, said first channel further comprising a first ledge, a second ledge, and a central cut-away portion.

21. The medical guide wire torquer of claim 20, wherein said internal cavity extends from said top into said central body portion.

22. The medical guide wire torquer of claim 21, wherein said first channel is positioned approximately equal distances between said top and said bottom.

23. The medical guide wire torquer of claim 22, further comprising a plurality of elastomers disposed in said cavity proximate to said bottom.

24. The medical guide wire torquer of claim 23, wherein said elastomers alternatively compress and expand, permitting adjustable positioning of said button within said cavity.

25. The medical guide wire torquer of claim 24, said second channel comprising a leading edge proximate to said first ledge and a trailing edge proximate to said second ledge.

26. The medical guide wire torquer of claim 25, wherein said button has a grasping position when said elastomers are expanded, defined by the positioning of the leading edge of the second channel proximate to, and elevated with respect to the first ledge of the first channel and the positioning of the trailing edge of the second channel proximate to, and elevated with respect to the second ledge of the first channel.

27. The medical guide wire torquer of claim 26, wherein said button has a release position when said elastomers are compressed, defined by the positioning of the leading edge of the second channel proximate to, and in substantial alignment with, the first ledge of the first channel and the positioning of the trailing edge of second channel proximate to, and in substantial alignment with, the second ledge of the first channel.

28. The medical guide wire torquer of claim 27, wherein said elastomers are expanded at an at-rest position, thereby positioning the button in a grasping position relative to the body.

29. The medical guide wire torquer of claim 28, said fastener further comprising a pin positioned in each of said apertures, each of said pins being adjustably positioned in one of said slots.

30. The medical guide wire torquer of claim 29, wherein said first channel and said second channel are adapted to releasably engage said medical guide wire.

31. The medical guide wire torquer of claim 30, wherein said body is elongate being substantially cylindrical in shape.

32. The medical guide wire torquer of claim 31, said body further comprising an exterior texture grasping surface.

* * * * *